(12) United States Patent
Tran et al.

(10) Patent No.: US 8,464,588 B2
(45) Date of Patent: Jun. 18, 2013

(54) WIRELESS ACOUSTIC INTERROGATION OF A PACKAGED MEDICAL IMPLANT

(75) Inventors: Binh C. Tran, Minneapolis, MN (US); Thomas W. Piaget, St. Paul, MN (US)

(73) Assignee: Cardiac Pacemaker, Inc., St. Paul, MN (US)

( * ) Notice: Subject to any disclaimer, the term of this patent is extended or adjusted under 35 U.S.C. 154(b) by 343 days.

(21) Appl. No.: 12/833,581

(22) Filed: Jul. 9, 2010

(65) Prior Publication Data

US 2011/0041613 A1 Feb. 24, 2011

Related U.S. Application Data

(60) Provisional application No. 61/235,407, filed on Aug. 20, 2009.

(51) Int. Cl.
*G01N 29/2475* (2006.01)
(52) U.S. Cl.
USPC ............................................. 73/632; 73/644
(58) Field of Classification Search
USPC ........ 73/622, 644, 632; 600/300, 301; 607/32
See application file for complete search history.

(56) References Cited

U.S. PATENT DOCUMENTS

| 4,423,732 | A | 1/1984 | Tarjan et al. |
| 4,605,007 | A | 8/1986 | Heraly |
| 5,237,991 | A | 8/1993 | Baker, Jr. et al. |
| 6,292,697 | B1 | 9/2001 | Roberts |
| 6,764,446 | B2 | 7/2004 | Wolinsky et al. |
| 7,563,142 | B1 | 7/2009 | Wenger et al. |
| 2005/0075695 | A1 | 4/2005 | Schommer |
| 2007/0119741 | A1 | 5/2007 | Wenger et al. |
| 2007/0123947 | A1 | 5/2007 | Wenger et al. |
| 2007/0162090 | A1 | 7/2007 | Penner |

FOREIGN PATENT DOCUMENTS

WO WO2005123186 A1 12/2005

*Primary Examiner* — J M Saint Surin
(74) *Attorney, Agent, or Firm* — Faegre Baker Daniels LLP

(57) ABSTRACT

Systems and methods of acoustically interrogating a packaged medical implant such as an implantable sensor are disclosed. An illustrative system includes a sterilizable package including a package tray and a cover, a sensor module disposed within the package, and an acoustic coupling member disposed within an interior space of the package tray. An external interrogator located outside of the sealed package can be used to acoustically communicate with the sensor module.

20 Claims, 14 Drawing Sheets

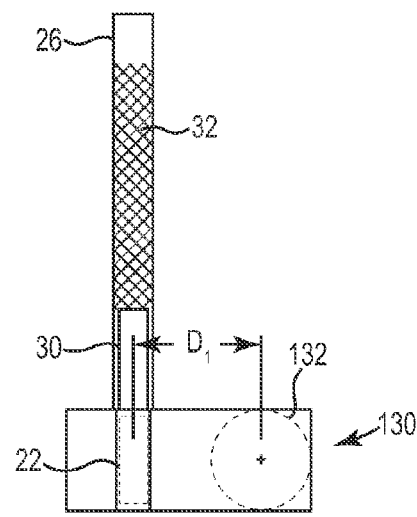
Fig. 12
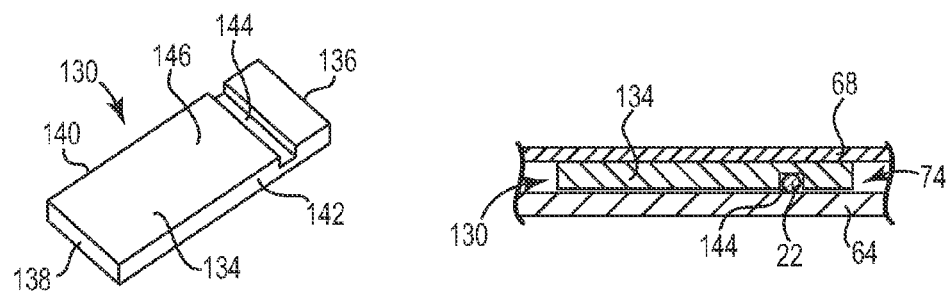
Fig. 13
Fig. 14

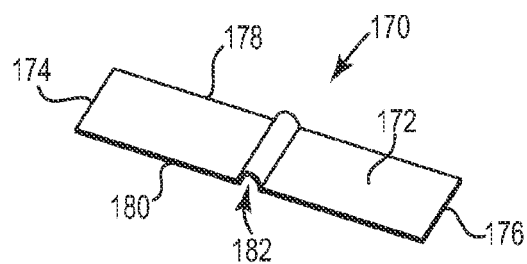
Fig. 18
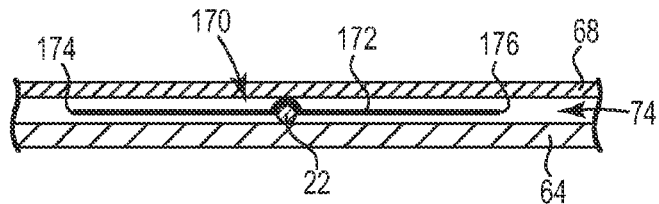
Fig. 19
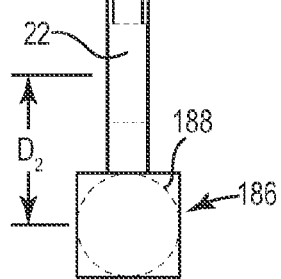
Fig. 20
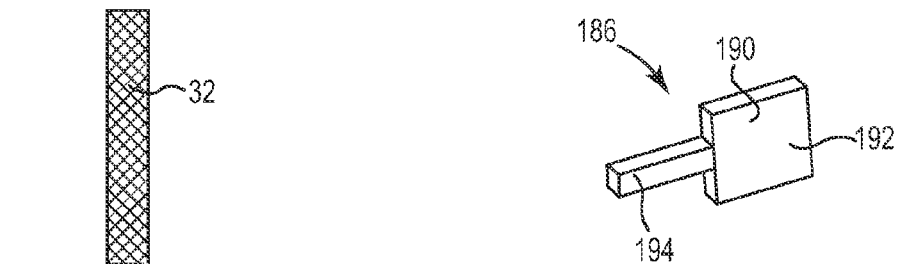
Fig. 21
Fig. 22

WIRELESS ACOUSTIC INTERROGATION OF A PACKAGED MEDICAL IMPLANT

CROSS-REFERENCE TO RELATED APPLICATIONS

This application claims the benefit under 35 U.S.C. §119 of U.S. Provisional Application No. 61/235,407, filed Aug. 20, 2009, entitled "Wireless Acoustic Interrogation of a Packaged Medical Implant," which is incorporated herein by reference in its entirety for all purposes.

TECHNICAL FIELD

The present invention relates generally to implantable medical devices. More specifically, the present invention relates to systems and methods of acoustically interrogating a packaged medical implant.

BACKGROUND

Implantable medical devices (IMDs) such as cardiac pacemakers, cardioverter/defibrillators, leads, and sensors are typically placed in a sterilized package by the manufacturer prior to being removed and implanted within the body. An example of a sterilized package is a blister pack, which typically includes an inner tray or pouch and a cover that seals the IMD within an interior form or chamber. The IMD is often sterilized while in the inner tray or pouch using steam, gas, ultraviolet light, or other suitable sterilization technique. A sterilization barrier such as a peelable or tearable seal can be opened to break the barrier, allowing the IMD to be removed and subsequently implanted into the patient. In some cases, other components may also be removed from the sterilized packaging for use in preparing the IMD for implantation.

For some types of IMDs, it may be desirable to test the operation and functionality of the IMD prior to breaking the sterilization barrier, while the IMD is still within the packaging. For an implantable sensor configured for insertion within the body, for example, it may be desirable to test the operation of the sensor prior to breaking the sterilization barrier and removing the sensor from the packaging. In the case of a pressure sensor, for example, it may be desirable to verify the accuracy and functionality of the pressure sensor while still in its packaging. In some cases, it may also be desirable to program the sensor, to verify the correct programming of the sensor, and/or to recharge a battery or to verify the battery capacity within the sensor prior to removal from the packaging.

In some cases, communication with IMDs located within the sterilized packaging can be difficult due to the complex communication pathway between the IMD and the device interrogating the IMD. For an IMD adapted to acoustically communicate with another device such as an external interrogator, for example, the presence of air or other gases in the acoustic pathway between the interrogator and the sensor can inhibit communication.

SUMMARY

The present invention relates to systems and methods of acoustically interrogating a packaged medical implant configured to communicate wirelessly via an acoustic link.

In Example 1, a system for acoustically interrogating an implantable medical device sealed within a package comprises: a sterilizable package; an implantable medical device disposed within the sterilizable package, the implantable medical device including an acoustic transducer configured to transmit and receive ultrasonic pulses; and a means for acoustically coupling the implantable medical device to an external interrogator disposed outside of the package, the acoustic coupling means configured to provide a conduit for propagation of the ultrasonic pulses through an interior space of the package. During acoustic interrogation, the acoustic coupling member is configured to provide a conduit for propagation of ultrasonic pulses transmitted and received through an interior space of the package. In some embodiments, for example, the acoustic coupling member provides a solid propagation medium or waveguide between a housing of the implantable medical device and the external interrogator. The acoustic coupling member allows propagation of the ultrasonic pulses between the devices by reducing impedance mismatches between the packaging, the device, and any medium interior or exterior to the packaging.

In Example 2, the system according to Example 1, wherein the implantable medical device includes a housing that contains the acoustic transducer, and wherein the acoustic coupling means forms a solid medium interface or solid medium waveguide between the housing and the external interrogator.

In Example 3, the system according to any of Examples 1-2, wherein the acoustic coupling means includes an acoustic coupling member.

In Example 4, the system according to Example 3, wherein the acoustic coupling member comprises an insert coupled to the implantable medical device and an interior surface of the packaging.

In Example 5, the system according to Example 4, wherein the acoustic coupling member includes a channel adapted to frictionally receive at least a portion of the housing.

In Example 6, the system according to Example 4, wherein the acoustic coupling member includes a first section disposed vertically adjacent to an acoustic transducer of the external interrogator, and a second section in contact with the housing.

In Example 7, the system according to Example 4, wherein the acoustic coupling member includes a first member hingedly coupled to a second member, the first and second members configured to engage the sensor housing.

In Example 8, the system according to Example 4, wherein the acoustic coupling member includes a plurality of wedges configured to engage the housing.

In Example 9, the system according to Example 4, wherein the acoustic coupling member includes a lower member and an upper member, at least one of the lower or upper members including a channel configured to receive the housing.

In Example 10, the system according to Example 4, wherein the acoustic coupling member includes a pad adapted to contact an inner surface of the cover.

In Example 11, the system according to Example 10, wherein the pad is disposed vertically adjacent to the housing within the package.

In Example 12, the system according to Example 10, wherein the pad is laterally offset from the housing within the package.

In Example 13, the system according to Example 10, wherein the pad is longitudinally offset from the housing within the package.

In Example 14, the system according to Example 2, wherein the acoustic coupling means includes a number of bump-outs on a sidewall of the package tray, the bump-outs configured to frictionally engage the housing.

In Example 15, a system for acoustically interrogating an implantable medical device sealed within a package comprises: a sterilizable package; a sensor module disposed within the sterilizable package, the sensor module including a sensor housing adapted to contain an acoustic transducer configured to acoustically communicate with an external interrogator; an acoustic coupling member disposed within an interior space of the package tray, the acoustic coupling member including a channel adapted to frictionally receive the sensor housing and a pad adapted to engage a surface of the package; and wherein the acoustic coupling member provides a solid medium interface for ultrasonic pulses transmitted in the interior space between the sensor housing and the external interrogator.

In Example 16, the system according to Example 15, wherein the pad is disposed vertically adjacent to the sensor housing within the package.

In Example 17, the system according to Example 15, wherein the pad is laterally offset from the sensor housing within the package.

In Example 18, the system according to Example 15, wherein the pad is longitudinally offset from the sensor housing within the package.

In Example 19, a method of acoustically interrogating a medical implant sealed within a sterilizable package comprises: coupling a medical implant including an acoustic transducer to an acoustic coupling member; inserting the implant and acoustic coupling member into a recess or cavity of a sterilizable package; sealing the implant within the package; and transmitting ultrasonic pulses between the sealed implant and an external interrogator disposed outside of the package.

In Example 20, the method according to Example 19, wherein the acoustic coupling member provides a conduit for propagation of the ultrasonic pulses through an interior space of the package.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 12 is a top schematic view showing another illustrative acoustic coupling member used to acoustically couple a sensor module disposed within a sterilized package to an external interrogator;

FIG. 13 is a perspective view showing the acoustic coupling member of FIG. 12 in greater detail;

FIG. 14 is a cross-sectional view showing the acoustic coupling member of FIG. 13 coupled to a sensor module within a sealed package tray;

FIG. 18 is a perspective view showing another illustrative acoustic coupling member used to acoustically couple a sensor module disposed within a sterilized package to an external interrogator;

FIG. 19 is a side cross-sectional view showing the acoustic coupling member of FIG. 18 acoustically coupled to the sensor module within a sealed package tray;

FIG. 20 is a top schematic view showing another illustrative acoustic coupling member used to acoustically couple a sensor module disposed within a sterilized package to an external interrogator;

FIG. 21 is a perspective view showing the acoustic coupling member of FIG. 20 in greater detail;

FIG. 22 is a cross-sectional view showing the acoustic coupling member of FIG. 21 acoustically coupled to the sensor module within a sealed package tray;

Figure 1:
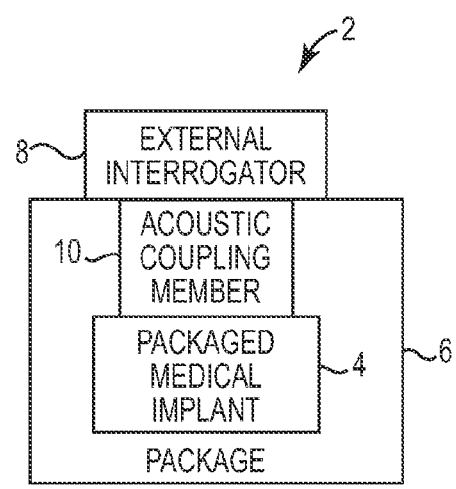
FIG. 1 is a block diagram showing an illustrative system for acoustically interrogating an implantable medical device sealed within a package.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a block diagram showing an illustrative system 2 for acoustically interrogating a packaged medical implant. In the embodiment shown, the system 2 includes an implantable medical device 4 disposed within a sealed package 6, an external interrogator 8 configured to transmit and receive ultrasonic pulses to and from the packaged implant 4, and an acoustic coupling member 10 configured to provide a conduit for propagation of the ultrasonic pulses through an interior space of the package 6 between the packaged implant 4 and the external interrogator 8.

The acoustic coupling member 10 is configured to provide a solid medium interface or waveguide between the packaged implant 4 and the external interrogator 8, replacing the air or gas in the acoustic pathway between the implant 4 and interrogator 8 that can inhibit transmission of ultrasonic pulses back and forth between the two devices. In some embodiments, and as discussed further herein, the acoustic coupling member 10 may facilitate acoustic communications back and forth between the packaged implant 4 and the external interrogator 8, allowing the implant 4 to be acoustically interrogated while still sealed within the package 6.

The packaged implant 4 can comprise any number of different medical devices that are typically sealed within medical packaging, and which are configured to acoustically communicate with the external interrogator 8 and/or one or more other devices via an acoustic link. Implantable medical devices that can be acoustically interrogated using the system can include, but are not limited to, implantable sensors, implantable pulse generators such as pacemakers and cardioverter/defibrillators, and implantable microstimulators. Other packaged devices can also be acoustically interrogated using the system.

Figure 2A:
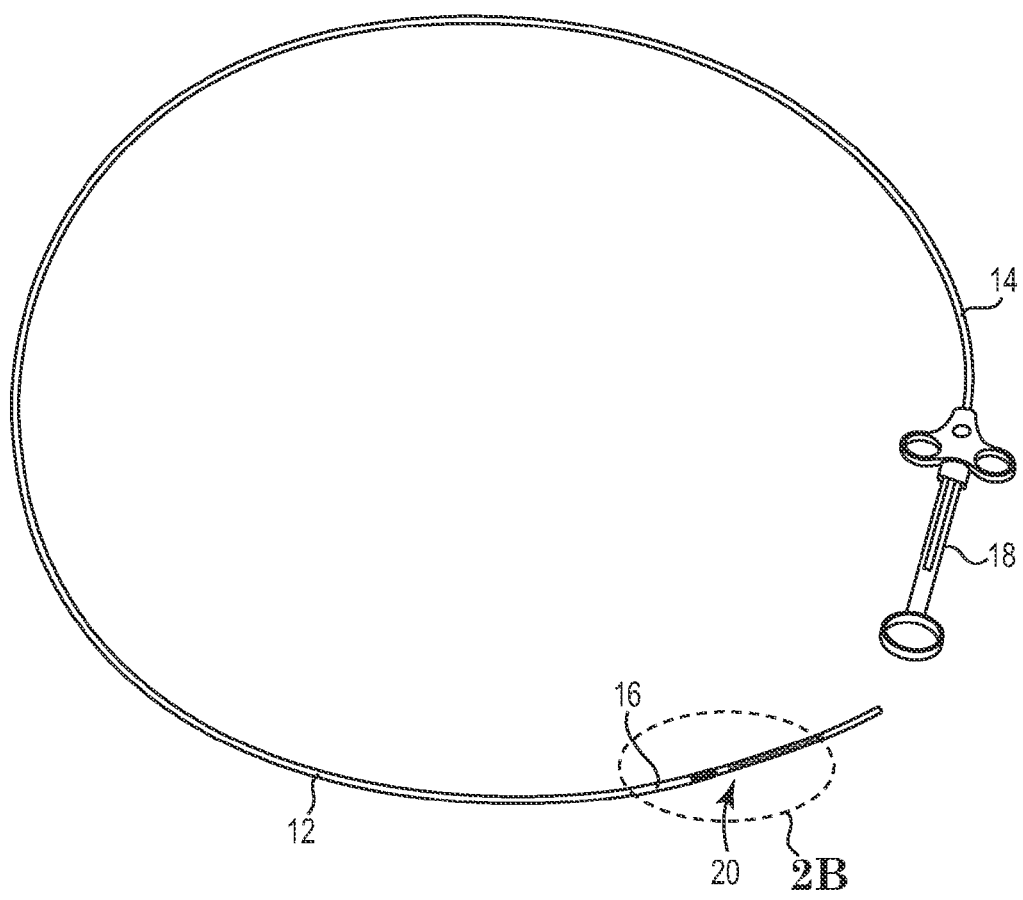
FIG. 2A is a perspective view of an implantable assembly configured for implantation within the body of a patient.

FIG. 2A is a perspective view of an implantable assembly configured for implantation within the body of a patient. The assembly, illustratively an implantable blood pressure sensor assembly configured for implantation within the heart or cardiac vasculature, includes a delivery catheter 12 having a proximal section 14 and a distal section 16. The proximal section 14 of the catheter 12 is coupled to an actuator handle 18 which, during implantation of the assembly within the body, can be actuated by a clinician to position and deploy a sensor assembly 20 within the body. In certain embodiments, for example, the sensor assembly 20 comprises a blood pressure sensing assembly that can be deployed out from the distal section 16 of the catheter 12 into an artery or vein (e.g., a pulmonary artery) leading into or from the heart, or alternatively within one of the atria or ventricles of the heart for sensing blood pressure. The sensor assembly 20 can be configured to sense other physiologic parameters within the body including, but not limited to, temperature, position, activity, blood flow, impedance, respiration, and sound.

Figure 2B:
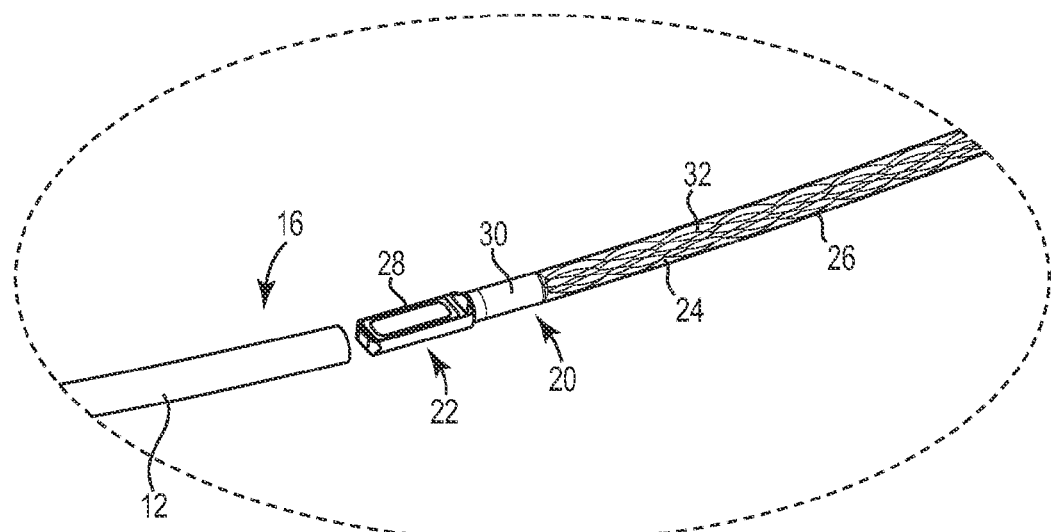
FIG. 2B is an enlarged view showing the sensor assembly of FIG. 2A in greater detail.

FIG. 2B is an enlarged view showing the sensor assembly 20 of FIG. 2A in greater detail. As further shown in FIG. 2B, the sensor assembly 20 includes a pressure sensor module 22 which, when packaged, is disposed in part within the interior lumen 24 of a loading tube 26. The sensor module 22 includes a sensor housing 28, a power supply housing 30, and an expandable fixation element 32, which, when deployed within the body at a target implantation site, is configured to radially expand from a collapsed position to an expanded position to anchor the sensor 22 within the body.

When situated in the device packaging, the sensor module 22 may be initially loaded into the interior lumen 24 of the loading tube 26, which serves to maintain the fixation element 32 in its collapsed position, and which facilitates loading of the sensor module 22 into the interior of the delivery catheter 12 subsequent to removal of the assembly from the packaging and prior to implantation within the body. Once the assembly is removed from the device packaging and loaded into the delivery catheter 12 in preparation for the implantation procedure, the loading tube 26 may then be discarded.

Figure 3:
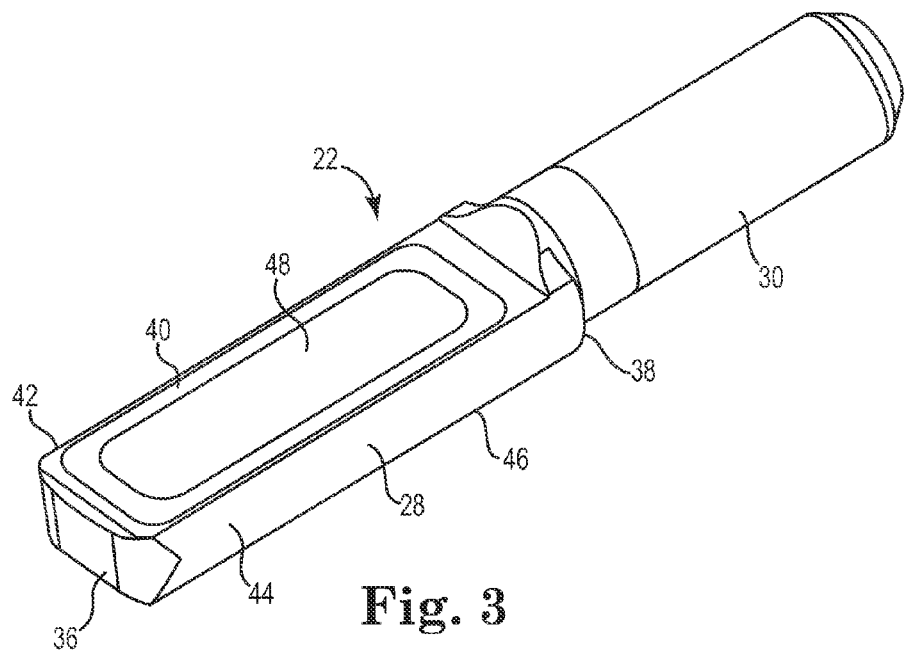
FIG. 3 is a perspective view showing the sensor housing and power supply housing of FIG. 2 in greater detail.

FIG. 3 is a perspective view showing the sensor housing 28 and power supply housing 30 of FIG. 2 in greater detail. As shown in FIG. 3, the sensor housing 28 includes a first end 36, a second end 38, and a number of sides 40,42,44,46. A flexible diaphragm 48 on one of the sides 40 is configured to displace in response to pressure exerted on the diaphragm 48 due to pulsitile blood flow at the implantation site.

The sensor housing 28 houses several sensor components, including a pressure sensor for sensing blood pressure, and an acoustic transducer for acoustically communicating sensor data and operational status information from the sensor module 22 to another implantable device and/or to an external interrogator located outside of the patient's body. An example of a sensor module 22 having an acoustic transducer for wirelessly communicating data is disclosed, for example, in U.S. Pat. No. 6,764,446, entitled, "Implantable Pressure Sensors and Methods For Making And Using Them," the content of which is incorporated herein by reference in its entirety for all purposes. The power supply housing 30 contains a power supply such as a battery or power capacitor that supplies power to the components within the sensor housing 28, including the pressure sensor and acoustic transducer.

Figure 4:
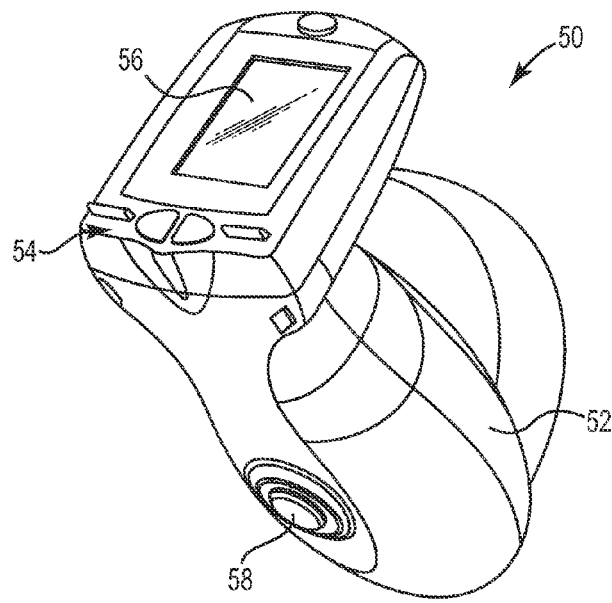
FIG. 4 is a perspective view showing an external interrogator that can be used to acoustically communicate with the sensor module of FIG. 3.

FIG. 4 is a perspective view showing an external interrogator 50 that can be used to acoustically communicate with the sensor module 22 of FIG. 3. In the embodiment of FIG. 4, the external interrogator 50 is a hand-held unit that can be used by a clinician to communicate with the sensor module 22 to monitor blood pressure data and operational status information. The external interrogator 50 includes a main body 52 that can be gripped by the clinician, a user interface 54 for inputting commands, and a display screen 54 that can be used to view sensor data obtained from the sensor module 22 as well as various operational parameters (e.g., battery status, communication status, etc.) associated with the module 22. An acoustic transducer 58 coupled to the main body 52 of the external interrogator 50 is used to establish an acoustic telemetry link with the sensor module 22. Further details regarding an exemplary body attachable hand-held interrogation unit is disclosed, for example, in U.S. patent application Ser. No. 11/373,005, entitled, "Body Attachable Unit In Wireless Communication With Implantable Devices," the content of which is incorporated herein by reference in its entirety for all purposes.

In certain embodiments, and as discussed further herein, the external interrogator 50 can be used to acoustically interrogate the sensor module 22 prior to removal of the module 22 from within its sterilized packaging. This may permit the clinician to acoustically interrogate the sensor module 22 without compromising the integrity of the sealed packaging or the sterility of the assembly 10 within the packaging. In some cases, for example, the external interrogator 50 can acoustically communicate with the sensor module 22 to verify that the module 22 is operating properly, for performing pre-implant testing, for providing various software and/or firmware upgrades to the module 22, for recharging a power supply within the power supply housing 30, or for performing some other desired function. In some embodiments, the external interrogator 50 may communicate with the sensor module 22 while in its sterilized packaging to verify that the acoustic transducer within the module 22 is operating properly, to take one or more sample pressure readings to verify that the pressure sensor is operating properly, and/or to take one or more sample temperature readings that can be used to calibrate the pressure readings taken by the pressure sensor within the sterilized packaging. The external interrogator 50 can also be configured to prompt the sensor module 22 to perform other commands and/or to perform other testing procedures while disposed within the sterilized packaging. In some cases, the ability to interrogate the sensor module 22 within its sterilized packaging may reduce in-patient testing procedures normally performed after the module 22 has been implanted within the body.

Figure 5:
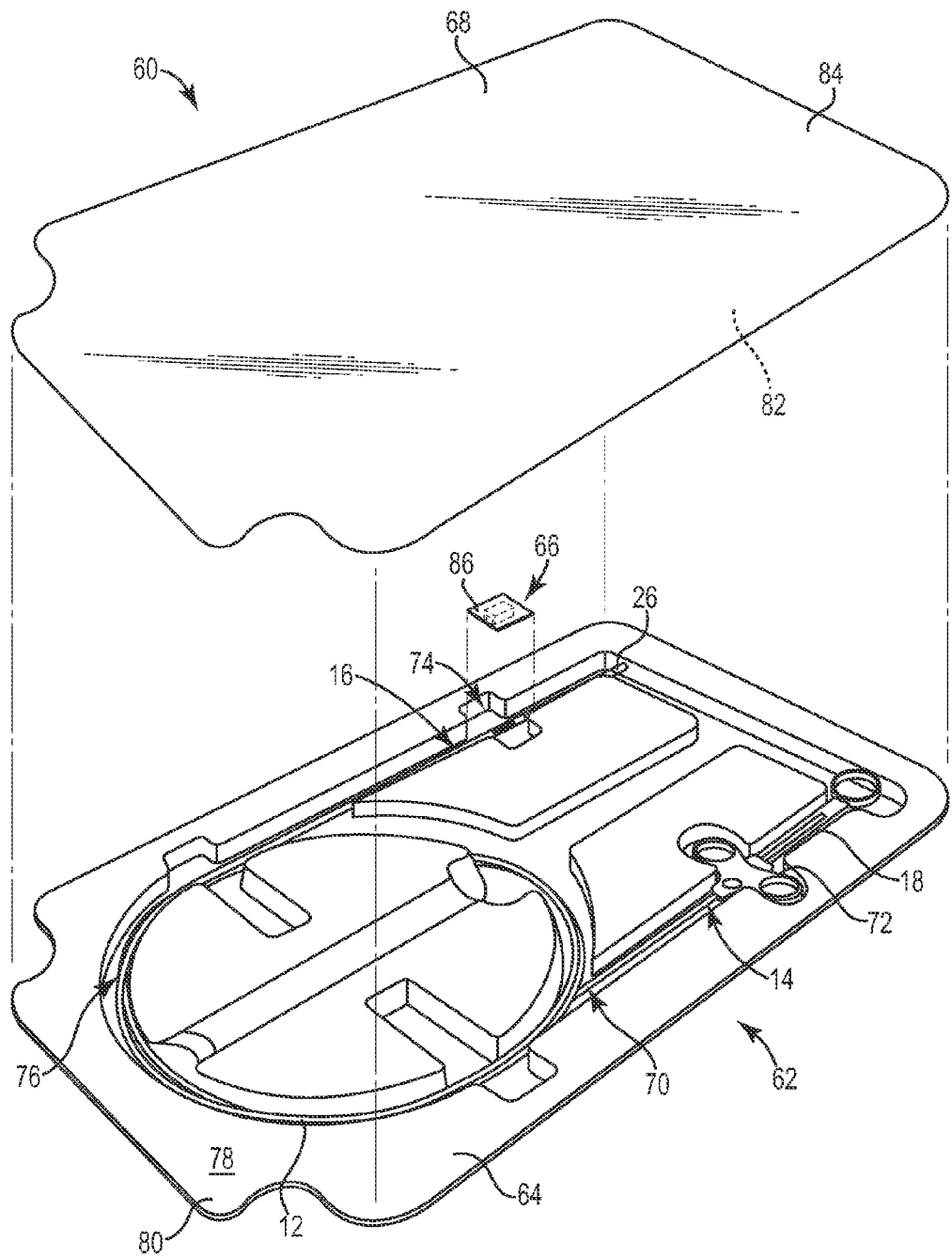
FIG. 5 is an assembly view showing an illustrative packaging system that can be acoustically interrogated using the external interrogator of FIG. 4.

FIG. 5 is an assembly view showing an illustrative packaging system 60 that can be acoustically interrogated using a device such as the external interrogator 50 of FIG. 4. In the embodiment of FIG. 5, the packaging system 60 includes a sterilizable package 62 including a package tray 64 such as a blister pack or pouch, an acoustic coupling member 66, and a cover 68. The package tray 64 can include a number of recessed regions defining a cavity 70 formed to match the contours of an assembly placed therein, as shown. A first recessed region 72, for example, supports the actuator handle 18 on the delivery catheter 12. A second recess region 74, in turn, supports the sensor module 22. A recessed channel 76 extending along the length of the assembly 10 supports the delivery catheter 12 and loading tube 26.

The package tray 64 has an inner surface 78 which, in addition to cavity 70, may form other recesses or cavities for containing accessories, tools, or other components packaged with the assembly 10. A number of blisters or bump-outs along the channel 76 or in the recessed regions 72,74 provide further gripping support for the package contents. In some embodiments, the package tray 64 may be fabricated from a polymeric material such as high-density polyethylene, which is capable of withstanding the sterilization procedures typically used to sterilize the package contents.

The package tray 64 includes a seal perimeter 80 along the inner surface 78 onto which the cover 68 is sealed after the assembly and any other package contents are placed into the tray 64. The cover 68 includes an inner surface 82 and outer surface 84. In some embodiments the cover 68 can be formed from coated paper such as TYVEK®, or from a high-density polymer.

The acoustic coupling member 66 is configured in size and shape to fit snugly within the recess 74 adjacent to the sensor module 22, and can be fabricated from a number of different metals, polymers, or metal-polymer composites. Examples of suitable materials that can be used include, but are not limited to, acrylic, ESD acetal, polytetrafluoroethylene, aluminum, and stainless steel.

A top portion 86 of the acoustic coupling member 66 is configured to closely contact the inner surface 82 of the cover 68, forming an acoustic pathway between the cover 68 and the sensor module 22 when the external interrogator 50 is placed against the outer surface 84 of the cover 68 to acoustically interrogate the module 22. In certain embodiments, for example, the acoustic coupling member 66, when situated between the inner surface 78 of the cover 68 and the sensor module 22, provides a solid medium interface between the external interrogator 50 and the sensor 22, replacing air or gas within that region of the package 62 that can inhibit transmission of ultrasonic pulses back and forth between the external interrogator 50 and the sensor module 22.

Figure 6:
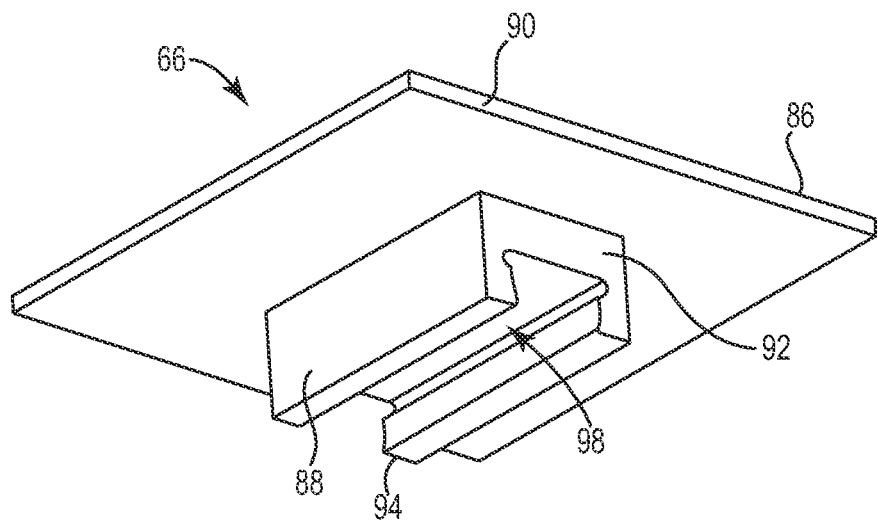
FIG. 6 is a perspective view showing the acoustic coupling member of FIG. 5 in greater detail.

FIG. 6 is a perspective view showing the acoustic coupling member 66 of FIG. 5 in greater detail. As further shown in FIG. 6, the acoustic coupling member 66 includes a main receiver body 88 and a pad 90. The main receiver body 88 has a first end 92, a second end 94, and a channel 98 that extends through the body 88 between the ends 92,94. The channel 98 is configured in size and shape to frictionally receive a portion of the sensor module 22 therein when situated within the recess 74 of the package tray 64.

Figure 7:
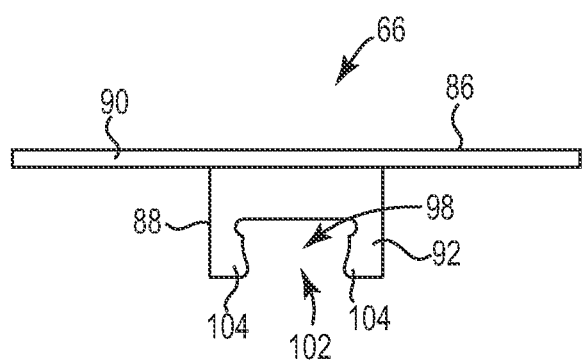
FIG. 7 is an end view of the acoustic coupling member of FIG. 6.

FIG. 7 is an end view of the acoustic coupling member 66 of FIG. 5. As further shown in conjunction with FIGS. 6-7, the channel 98 is sized and shaped to frictionally receive the sensor housing 28. A lower portion 102 of the channel 98 is configured to cradle the sides 42,44,46 of the sensor housing 48. In some embodiments, an inwardly extending portion 104 of the main receiver body 88 is configured to bend or flex slightly when the sensor housing 48 is inserted into the lower portion of the channel 98, allowing the sensor housing 48 to be snap-fit into the channel 98.

Figure 8:
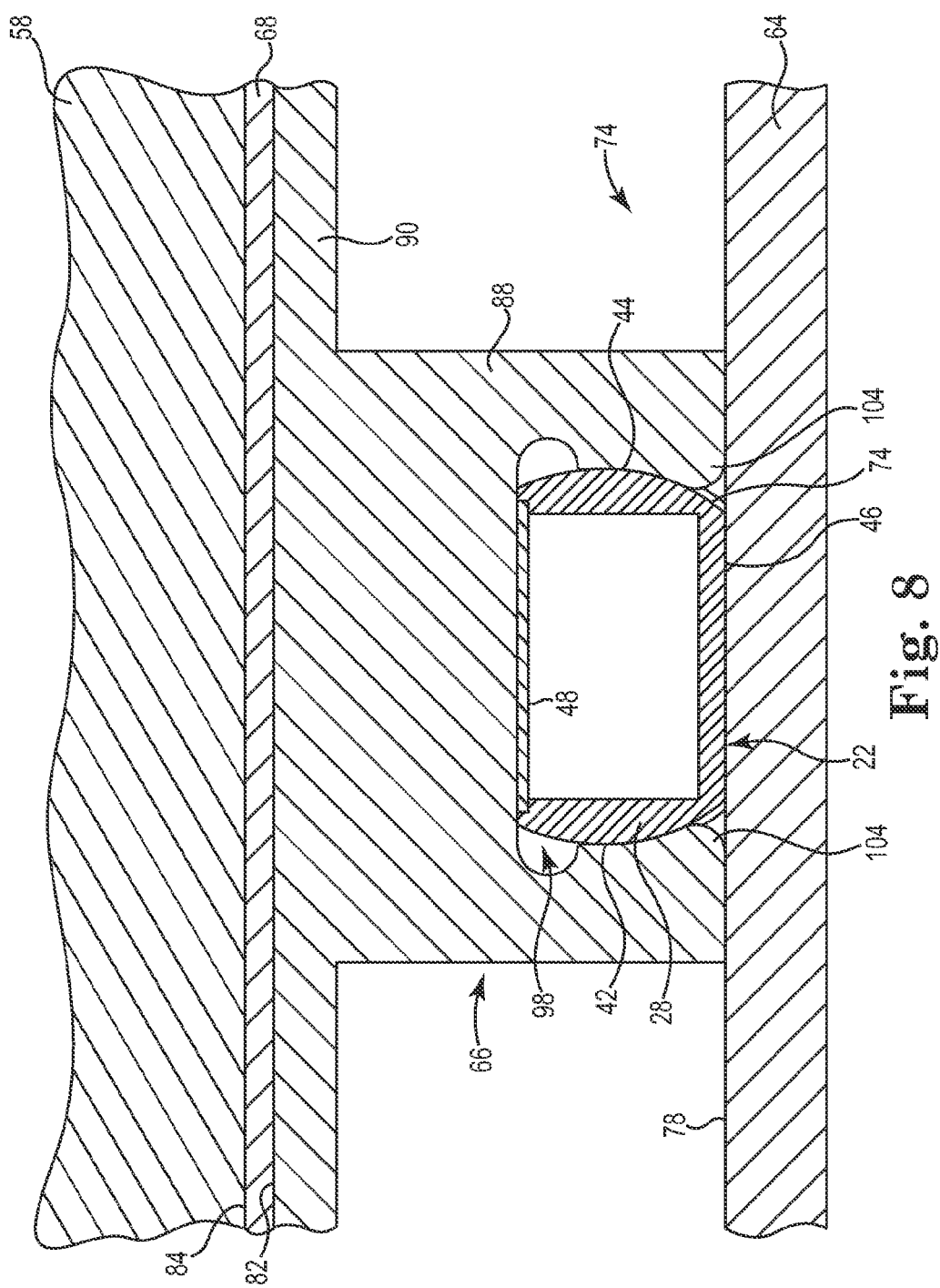
FIG. 8 is an end cross-sectional view showing the acoustic coupling member of FIG. 7 coupled to the sensor module within the sealed package tray.

FIG. 8 is an end cross-sectional view showing the acoustic coupling member 66 of FIG. 7 coupled to the sensor module 22 within the sealed package tray 64. As shown in FIG. 8, the acoustic transducer 58 for the external interrogator 50 can be placed over the outer surface 84 of the cover 68 at a location adjacent to the recess 74 that supports the acoustic coupling member 66 and the sensor housing 28. In an alternative embodiment shown in FIG. 9, the acoustic transducer 58 for the external interrogator 50 can be placed over an outer surface 106 of the package tray 64 at a location adjacent to the recess 74 that supports the acoustic coupling member 66 and the sensor housing 28. Due to the presence of the acoustic coupling member 66 within the recess 74, a solid medium exists between the sensor housing 28 and the acoustic transducer 58, serving as a conduit for propagation of ultrasonic pulses between the external interrogator 50 and the sensor module 22.

Figure 10:
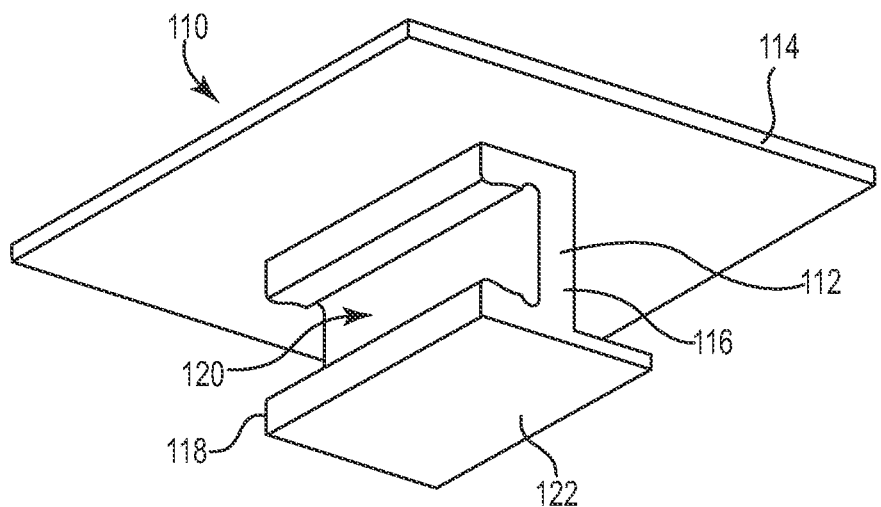
FIG. 10 is a perspective view showing an acoustic coupling member in accordance with another illustrative embodiment.

FIG. 10 is a perspective view showing an acoustic coupling member 110 in accordance with another illustrative embodiment. As shown in FIG. 10, the acoustic coupling member 110 includes a main receiver body 112 and a pad 114. The main receiver body 112 has a first end 116, a second end 118, and a channel 120 that extends through the body 112 between the ends 116,118. The channel 120 is configured in size and shape to frictionally receive a portion of the sensor module 22 therein when situated within the recess 74 of the package tray 64. A second pad 122 on the lower portion of the main receiver body 112 is configured to engage the inside surface 78 of the package tray 64.

Figure 9:
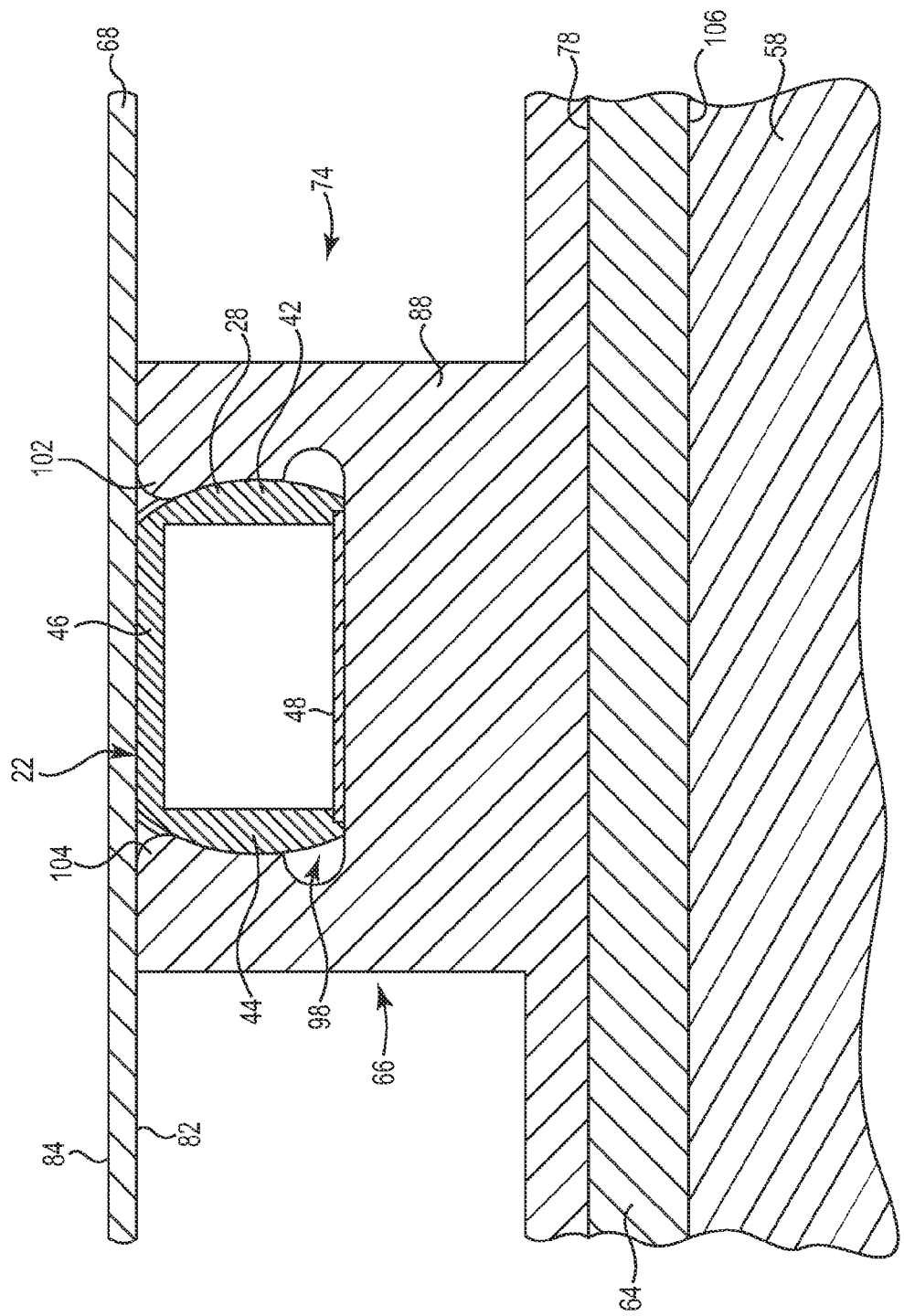
FIG. 9 is another end cross-sectional view showing the acoustic coupling member of FIG. 7 coupled to the sensor module, wherein the acoustic transducer for the external interrogator is placed over an outer surface of the package tray.
Figure 11:
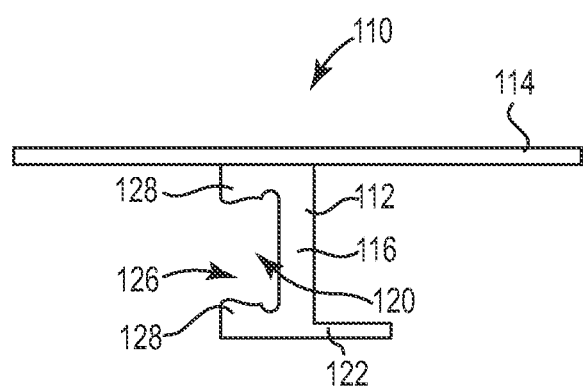
FIG. 11 is an end view of the acoustic coupling member of FIG. 10.

FIG. 11 is an end view of the acoustic coupling member 110 of FIG. 10. As further shown in conjunction with FIGS. 10-11, the channel 120 is sized and shaped to frictionally receive the sensor housing 28, similar to the acoustic coupling member 66 discussed above. In the embodiment of FIGS. 9-10, however, the channel 120 is oriented such that the sensor housing 28 is supported sideways within the package tray 64. An outer portion 126 of the channel 120 is configured to cradle the other sides 42,44,46 of the sensor housing 48. An inwardly extending portion 128 of the main receiver body 112 is configured to bend or flex slightly when the sensor housing 48 is inserted into the outer portion 126 of the channel 120, allowing the sensor housing 48 to be snap-fit into the channel 120.

FIG. 12 is a top schematic view showing another illustrative acoustic coupling member 130 used to acoustically couple a sensor module 22 disposed within a sealed package tray to an external interrogator. As shown in FIG. 12, the acoustic coupling member 130 comprises an insert adapted to couple to the sensor module 22 within the interior of the packaging. In some embodiments, for example, the acoustic coupling member 130 is configured to overlie the sensor module 22 within the recess 74 of the package tray 64 shown in FIG. 5.

In the embodiment of FIG. 12, the external interrogator transducer 58 can be placed over a region 132 of the acoustic coupling member 130 laterally offset a distance $D_1$ from the sensor module 22. In some embodiments, for example, the external interrogator transducer 58 can offset a distance $D_1$ of between about 1 cm to about 5 cm from the sensor module 22, although other distances are possible. In use, this offset distance $D_1$ permits the external interrogator transducer 58 to be placed over the cover 68 without having to precisely align the transducer 58 with the sensor module 22 during interrogation. In some package configurations, this may permit the external interrogator transducer 58 to be relocated to a more convenient location on the packaging for interrogation, and serves to increase the contact surface area over which the acoustic interrogation can be performed.

FIG. 13 is a perspective view showing the acoustic coupling member 130 of FIG. 12 in greater detail. As shown in FIG. 13, the acoustic coupling member 130 can be configured as a waveguide for acoustic communications between the sensor module 22 and the external interrogator transducer 58. The acoustic coupling member 130 includes a rectangular-shaped body 134 having a first end 136, a second end 138, a first side 140, and a second side 142. A channel 144 inset within a bottom section 146 of the body 134 extends across the width of the body 134 between the sides 140,142. The channel 144 is configured in size and shape to frictionally receive a portion of the sensor module 22 therein when situated within the package tray 64.

FIG. 14 is a cross-sectional view showing the acoustic coupling member 130 of FIG. 13 coupled to a sensor module 22 within a sealed package tray 64. As shown in FIG. 14, the acoustic coupling member 130 is configured to support the sensor module 22 within the recess 74 of the package tray 64. During acoustic interrogation, the acoustic coupling member 130 serves as a solid medium waveguide between the sensor module 22 and the acoustic transducer 58 of the external interrogator 50. In some packaging configurations, this allows the contact point of the transducer 58 to be relocated to a different location.

Figure 15:
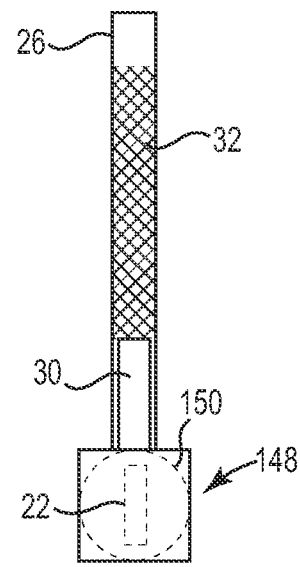
FIG. 15 is a top schematic view showing another illustrative acoustic coupling member used to acoustically couple a sensor module disposed within a sterilized package to an external interrogator.

FIG. 15 is a top schematic view showing another illustrative acoustic coupling member 148 used to acoustically couple a sensor module 22 disposed within a sealed package tray to an external interrogator. As shown in FIG. 15, the acoustic coupling member 148 comprises an insert adapted to couple to a sensor module 22 within the interior of the packaging. In some embodiments, for example, the acoustic coupling member 148 is configured to overlie the sensor module 22 within the package tray 64 shown in FIG. 5. In the embodiment of FIG. 15, the external interrogator transducer 58 can be placed over a region 150 of the acoustic coupling member 148 vertically adjacent to the sensor module 22.

Figure 16:
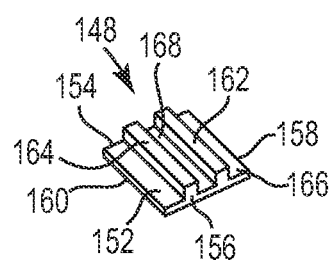
FIG. 16 is a perspective view showing the acoustic coupling member of FIG. 15 in greater detail.

FIG. 16 is a perspective view showing the acoustic coupling member 148 of FIG. 15 in greater detail. As further shown in FIG. 16, the acoustic coupling member 148 includes a body 152 having a first end 154, a second end 156, a first side 158, and a second side 160. A number of vanes 162,164 on the bottom section 166 of the body 152 form a channel 168 configured in size and shape to frictionally receive a portion of the sensor module 22 therein when situated within the package tray 64.

Figure 17:
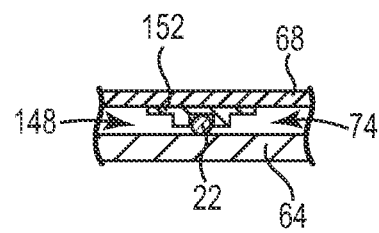
FIG. 17 is a cross-sectional view showing the acoustic coupling member of FIG. 16 acoustically coupled to a sensor module within a sealed package tray.

FIG. 17 is a cross-sectional view showing the acoustic coupling member 148 of FIG. 16 coupled to a sensor module 22 within a sealed package tray 64. As shown in FIG. 17, the acoustic coupling member 148 is configured to support the sensor module 22 within the package tray 64. During acoustic interrogation, the acoustic coupling member 148 serves as a solid medium interface between the sensor module 22 and the acoustic transducer 58 of the external interrogator 50.

FIG. 18 is a perspective view showing another illustrative acoustic coupling member 170 used to acoustically couple a sensor module 22 disposed within a sealed package tray to an external interrogator. As shown in FIG. 18, the acoustic coupling member 170 comprises an insert adapted to couple to the sensor module 22 within the interior of the packaging. In some embodiments, for example, the acoustic coupling member 170 is configured to overlie the sensor module 22 within the package tray 64 shown in FIG. 5.

The acoustic coupling member 170 includes a body 172 having a first end 174, a second end 176, a first side 178, and a second side 180. In some embodiments, the body 174 comprises a thin piece having a semi-circular channel 182 that extends across the width of the body 172 between the sides 178,180. The channel 182 is configured in size and shape to frictionally receive therein a portion of the sensor module 22.

FIG. 19 is a cross-sectional view showing the acoustic coupling member 170 of FIG. 18 coupled to the sensor module 22 within a sealed package tray 64. As shown in FIG. 19, the acoustic coupling member 170 is configured to support the sensor module 22 within the recess 74 of the package tray 64, and serves as a solid medium waveguide between the sensor module 22 and acoustic transducer 58 of the external interrogator 50.

FIG. 20 is a top schematic view showing another illustrative acoustic coupling member 186 used to acoustically couple a sensor module disposed within a sterilized package to an external interrogator. As shown in FIG. 20, the acoustic coupling member 186 comprises an insert adapted to couple to a sensor module 22 within the interior of the packaging. In certain embodiments, for example, the acoustic coupling member 186 is configured to overlie the sensor module 22 within the package tray 64 shown in FIG. 5.

In the embodiment of FIG. 20, the external interrogator transducer 58 can be placed over a region 188 of the acoustic coupling member 186 that is longitudinally offset a distance $D_2$ from the sensor module 22. In some embodiments, for example, the external interrogator transducer 58 can be offset a distance $D_2$ of between about 1 cm to about 5 cm from the sensor module 22, although other distances are possible. In use, this offset distance $D_2$ permits the external interrogator transducer 58 to be placed over the cover 68 without having to precisely align the transducer 58 with the sensor module 22 during interrogation. In some package configurations, this may permit the external interrogator transducer 58 to be relocated to a more convenient location on the packaging, and serves to increase the contact surface area over which the acoustic interrogation can be performed.

FIG. 21 is a perspective view showing the acoustic coupling member 186 of FIG. 20 in greater detail. As further shown in FIG. 21, the acoustic coupling member 186 includes a body 190 having a first section 192 and a second section 194. The first section 192 comprises a pad having a relatively large surface area, which serves to increase the area upon which the external interrogator transducer 58 can be acoustically coupled to the acoustic coupling member 186. The second section 194, in turn, has a relatively small surface area configured to overlie the sensor module 22.

FIG. 22 is a cross-sectional view showing the acoustic coupling member 186 of FIG. 21 acoustically coupled to a sensor module 22 within a sealed package tray 64. As shown in FIG. 22, the acoustic coupling member 186 is configured to overlie a portion of the loading tube 26, which in some embodiments can be positioned between the sensor module 22 and the acoustic coupling member 186. During acoustic interrogation, the acoustic coupling member 186 serves as a solid medium interface between the sensor module 22 and the acoustic transducer 58 of the external interrogator 50, providing an acoustic conduit at the point of contact 196 to the cover 68 and to the loading tube 26 containing the sensor module 22.

Figure 23:
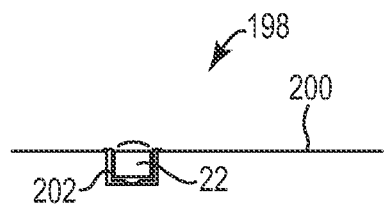
FIG. 23 is a side view showing an acoustic coupling member in accordance with another illustrative embodiment.

FIG. 23 is a side view showing another illustrative acoustic coupling member 198 used to acoustically couple a sensor module 22 disposed within a sealed package to an external interrogator. As shown in FIG. 23, the acoustic coupling member 198 comprises an insert adapted to couple to a sensor module 22 within the interior of the packaging. The acoustic coupling member 198 includes a body 200 with a channel 202 sized and shaped to frictionally receive the sensor module 22 therein when placed within the packaging. In the embodiment of FIG. 23, the channel 202 supports the underside and sides of the sensor module 22 within the packaging. During acoustic interrogation, the acoustic coupling member 198 serves as a solid medium waveguide between the sensor module 22 and the acoustic transducer 58 of the external interrogator 50.

Figure 24:
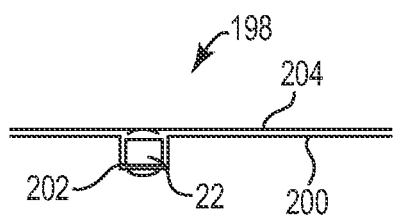
FIG. 24 is a side view showing an acoustic coupling member in accordance with another illustrative embodiment.

In some embodiments, and as further shown in FIG. 24, a slide member 204 can be configured to overlie the sensor module 22 and the body 200 of the acoustic coupling member 198 within the packaging. The slide member 204 comprises a relatively thin member that can be adjusted within the sealed packaging to offset the location where the external interrogator transducer 58 is placed against the packaging.

Figure 25:
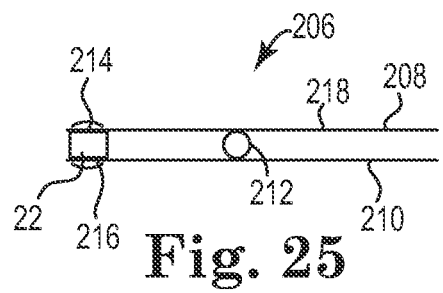
FIG. 25 is a side view showing an acoustic coupling member in accordance with another illustrative embodiment.

FIG. 25 is a side view showing another illustrative acoustic coupling member 206 used to acoustically couple a sensor module 22 disposed within a sealed package to an external interrogator. As shown in FIG. 25, the acoustic coupling member 206 comprises an insert adapted to couple to the sensor module 22 within the interior of the packaging. The acoustic coupling member 206 includes a first, upper member 208 hingedly coupled to a second, lower member 210 via a hinge 212. The first member 208 comprises a relatively thin member having an end 214 that engages an upper portion of the sensor module 22 within the packaging. The second member 210, in turn, comprises a relatively thin member having an end 216 that engages a lower portion of the sensor module 22 within the packaging. The ends 214,216 of the first and second members 208,210 are biased together via the hinge 212, thus frictionally engaging the sensor module 22 between the first and second members 208,210.

The acoustic transducer 58 of the external interrogator 50 can be positioned adjacent to a point 218 on the first member 208 that is laterally offset from the sensor module 22. During acoustic interrogation, the acoustic coupling member 206 serves as a solid medium waveguide between the sensor module 22 and the acoustic transducer 58 of the external interrogator 50.

Figure 26:
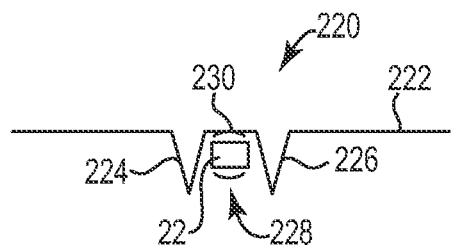
FIG. 26 is a side view showing an acoustic coupling member in accordance with another illustrative embodiment.

FIG. 26 is a side view showing another illustrative acoustic coupling member 220 used to acoustically couple a sensor module 22 disposed within a sealed package to an external interrogator. As shown in FIG. 26, the acoustic coupling member 220 comprises an insert adapted to couple to a sensor module 22 within the interior of the packaging. The acoustic coupling member 220 includes a body 222 with a number of V-shaped wedges 224,226 that form a channel 228 sized and shaped to frictionally receive therein a portion of the sensor module 22. The V-shaped wedges 224,226 are configured to frictionally engage the sides of the sensor module 22, thus securing the module 22 to the body 222. During acoustic interrogation, the acoustic coupling member 220 serves as a solid medium interface between the sensor module 22 and the acoustic transducer 58 of the external interrogator 50, providing an acoustic conduit at the point of contact 230 of the body 222 to the cover.

Figure 27:
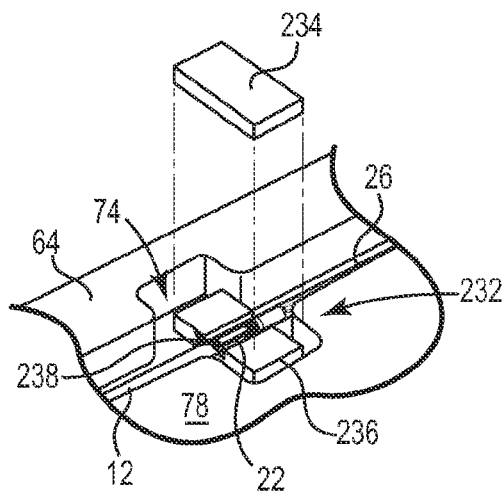
FIG. 27 is a schematic view showing an acoustic coupling member in accordance with another illustrative embodiment.

FIG. 27 is a schematic view showing another acoustic coupling member 232 used to acoustically couple a sensor module 22 disposed within a sealed package to an external interrogator. In the embodiment of FIG. 27, the acoustic coupling member 232 comprises an insert adapted to couple to a sensor module 22 within a sealed package tray 64. The acoustic coupling member 232 comprises a first, upper member 234 configured to overlie the sensor module 22, and a second, lower member 236 configured to cradle the underside of the sensor module 22, as shown. A channel 238 inset within the lower member 236 is sized and shaped to frictionally receive the sensor module 22 therein when situated within the package tray 64.

Figure 28:
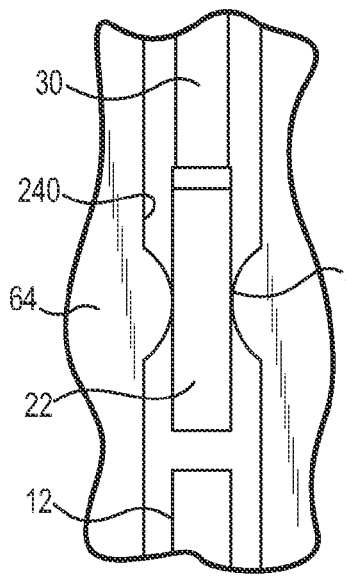
FIG. 28 is a top schematic view showing a package tray with sidewalls including a number of semi-circular bump-outs.
Figure 30:
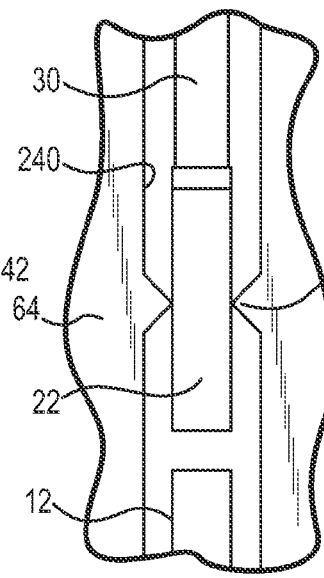
FIG. 30 is a top schematic view showing a package tray with sidewalls including a number of bump-outs in accordance with another illustrative embodiment.
Figure 31:
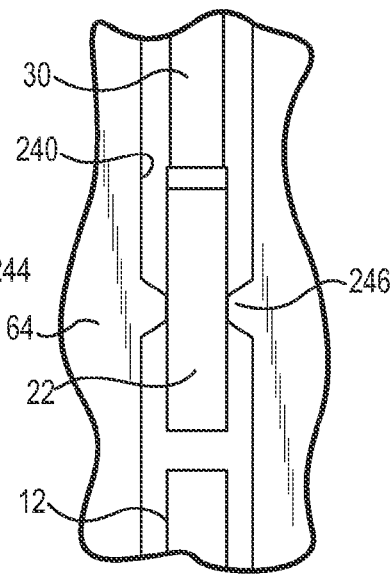
FIG. 31 is a top schematic view showing a package tray with sidewalls including a number of bump-outs in accordance with another illustrative embodiment.
Figure 29:
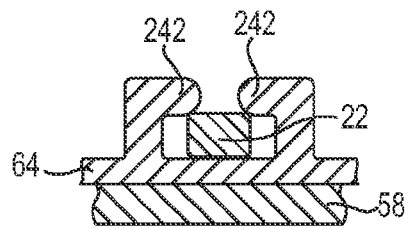
FIG. 29 is a cross-sectional view along line 29-29 in FIG. 28.

In certain embodiments, the package tray 64 itself may include one or more of the features described herein, which serve to acoustically couple the external interrogator 50 to the sensor module 22. In another embodiment shown in FIGS. 28-29, for example, the sidewalls 240 of a package tray 64 may include a number of semi-circular bump-outs 242 configured to frictionally engage the sensor module 22. During acoustic interrogation, the bump-outs 242 serve to acoustically couple the sensor module 22 to the acoustic transducer 58 of the external interrogator 50 through the package tray 64 itself. The bump-outs 242 also function to prevent movement of the sensor module 22 within the interior of the package tray 64. The bump-outs 242 may have a semi-circular shape, as shown in FIG. 28, or can comprise other desired shapes. FIGS. 30 and 31, for example, show several alternatively shaped bump-outs 244,246 configured to frictionally engage the sensor module 22. Other configurations are also possible.

Although various embodiments are described herein in the context of IMDs used to monitor cardiac function, and in particular blood pressure sensors, other types of implants can also be packaged and interrogated in accordance with other embodiments. Examples of other cardiac devices can include, but are not limited to, cardiac pacemakers, cardioverter/defibrillators, microstimulators, and implantable ECG recorders. In addition, other types of medical devices can also be packaged and interrogated in accordance with other embodiments.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for acoustically interrogating an implantable medical device sealed within a package, the system comprising:
   a sterilizable package;
   an implantable medical device disposed within the sterilizable package, the implantable medical device including an acoustic transducer configured to transmit and receive ultrasonic pulses; and
   a means for acoustically coupling the implantable medical device to an external interrogator disposed outside of the package, the acoustic coupling means configured to provide a solid conduit for propagation of the ultrasonic pulses through an interior space of the package.

2. The system of claim 1, wherein the implantable medical device includes a housing that contains the acoustic transducer, and wherein the acoustic coupling means forms a solid medium interface or solid medium waveguide between the housing and the external interrogator.

3. The system of claim 2, wherein the acoustic coupling means includes an acoustic coupling member.

4. The system of claim 3, wherein the acoustic coupling member comprises an insert coupled to the implantable medical device and an interior surface of the packaging.

5. The system of claim 4, wherein the acoustic coupling member includes a channel adapted to frictionally receive at least a portion of the housing.

6. The system of claim 4, wherein the acoustic coupling member includes a first section disposed vertically adjacent to an acoustic transducer of the external interrogator, and a second section in contact with the housing.

7. The system of claim 4, wherein the acoustic coupling member includes a first member hingedly coupled to a second member, the first and second members configured to engage the sensor housing.

8. The system of claim 4, wherein the acoustic coupling member includes a plurality of wedges configured to engage the housing.

9. The system of claim 4, wherein the acoustic coupling member includes a lower member and an upper member, at least one of the lower or upper members including a channel configured to receive the housing.

10. The system of claim 4, wherein the acoustic coupling member includes a pad adapted to contact an inner surface of the cover.

11. The system of claim 10, wherein the pad is disposed vertically adjacent to the housing within the package.

12. The system of claim 10, wherein the pad is laterally offset from the housing within the package.

13. The system of claim 10, wherein the pad is longitudinally offset from the housing within the package.

14. The system of claim 2, wherein the acoustic coupling means includes a number of bump-outs on a sidewall of the package tray, the bump-outs configured to frictionally engage the housing.

15. A system for acoustically interrogating an implantable medical device sealed within a package, the system comprising:
 a sterilizable package;
 a sensor module disposed within the sterilizable package, the sensor module including a sensor housing configured to contain an acoustic transducer configured to acoustically communicate with an external interrogator;
 an acoustic coupling member disposed within an interior space of the package tray, the acoustic coupling member including a channel adapted to frictionally receive the sensor housing and a pad configured to engage a surface of the package; and
 wherein the acoustic coupling member provides a solid medium interface for ultrasonic pulses transmitted in the interior space between the sensor housing and the external interrogator.

16. The system of claim 15, wherein the pad is disposed vertically adjacent to the sensor housing within the package.

17. The system of claim 15, wherein the pad is laterally offset from the sensor housing within the package.

18. The system of claim 15, wherein the pad is longitudinally offset from the sensor housing within the package.

19. A method of acoustically interrogating a medical implant sealed within a sterilizable package, the method comprising:
 coupling a medical implant including an acoustic transducer to a solid acoustic coupling member;
 inserting the implant and acoustic coupling member into a recess or cavity of a sterilizable package;
 sealing the implant within the package; and
 transmitting ultrasonic pulses between the sealed implant and an external interrogator disposed outside of the package.

20. The method of claim 19, wherein the acoustic coupling member provides a conduit for propagation of the ultrasonic pulses through an interior space of the package.

* * * * *